(12) United States Patent
Varadan et al.

(10) Patent No.: US 10,460,831 B2
(45) Date of Patent: Oct. 29, 2019

(54) PREDICTIVE OUTCOME ASSESSMENT FOR CHEMOTHERAPY WITH NEOADJUVANT BEVACIZUMAB

(71) Applicant: KONINKLIJKE PHILIPS N.V., Eindhoven (NL)

(72) Inventors: Vinay Varadan, New York, NY (US); Sitharthan Kamalakaran, Pelham, NY (US); Angel Janevski, New York, NY (US); Nilanjana Banerjee, Armonk, NY (US); Nevenka Dimitrova, Pelham Manor, NY (US); Lyndsay Harris, Briarcliff Manor, NY (US)

(73) Assignee: Koninklijke Philips N.V., Eindhoven (NL)

( * ) Notice: Subject to any disclaimer, the term of this patent is extended or adjusted under 35 U.S.C. 154(b) by 522 days.

(21) Appl. No.: 14/649,321

(22) PCT Filed: Nov. 22, 2013

(86) PCT No.: PCT/IB2013/060326
§ 371 (c)(1),
(2) Date: Jun. 3, 2015

(87) PCT Pub. No.: WO2014/087294
PCT Pub. Date: Jun. 12, 2014

(65) Prior Publication Data
US 2015/0347679 A1 Dec. 3, 2015

Related U.S. Application Data

(60) Provisional application No. 61/732,472, filed on Dec. 3, 2012.

(51) Int. Cl.
*C12Q 1/68* (2018.01)
*G16B 40/00* (2019.01)
(Continued)

(52) U.S. Cl.
CPC .......... *G16B 40/00* (2019.02); *A61K 39/3955* (2013.01); *A61K 45/06* (2013.01);
(Continued)

(58) Field of Classification Search
CPC ... G06F 19/24; G06F 19/704; A61K 39/3955; A61K 45/06; C07K 16/22; C12Q 1/6886
See application file for complete search history.

(56) References Cited

U.S. PATENT DOCUMENTS

| | | | |
|---|---|---|---|
| 2008/0248033 A1 | 10/2008 | Ferrara et al. | |
| 2011/0117083 A1* | 5/2011 | Bais ..................... | C12Q 1/6883 424/133.1 |
| 2012/0020959 A1 | 1/2012 | Desai et al. | |

FOREIGN PATENT DOCUMENTS

| | | |
|---|---|---|
| JP | 2007507222 A | 3/2007 |
| WO | 2004111603 A2 | 12/2004 |

(Continued)

OTHER PUBLICATIONS

Yang et al., (Clin Cancer Res. Sep. 15, 2008; 14(18): 5893-5899), (Year: 2008).*

(Continued)

*Primary Examiner* — Aaron A Priest (57) ABSTRACT

In a predictive outcome assessment test for predicting whether a patient undergoing a breast cancer treatment regimen will achieve pathological complete response (pCR), differential gene expression level information are generated for an input set of genes belonging to the TGF-β signaling pathway. The differential gene expression level information compares baseline gene expression level information from a baseline sample (70) of a breast tumor of a patient acquired before initiating (71) a breast cancer therapy regimen to the patient and response gene expression level information from a response sample (72) of the breast tumor acquired after initiating the breast cancer therapy regimen by administering (Continued)

a first dose of bevacizumab to the patient. A pCR prediction for the patient is computed based on the differential gene expression level information for the input set of genes belonging to the TGF-β signaling pathway. Related predictive outcome assessment test development methods are also disclosed.

12 Claims, 9 Drawing Sheets

(51) Int. Cl.
    A61K 39/395    (2006.01)
    C07K 16/22     (2006.01)
    A61K 45/06     (2006.01)
    G16C 20/30     (2019.01)
    C12Q 1/6886    (2018.01)

(52) U.S. Cl.
    CPC ............ *C07K 16/22* (2013.01); *C12Q 1/6886* (2013.01); *G16C 20/30* (2019.02); *C12Q 2600/106* (2013.01); *C12Q 2600/158* (2013.01)

(56) References Cited

FOREIGN PATENT DOCUMENTS

| WO | 2011020049 A1 | 2/2011 |
| WO | 2011153224 A2 | 12/2011 |
| WO | 2012106559 A1 | 8/2012 |

OTHER PUBLICATIONS

Agilent gene list found at https://www.chem.agilent.com/cag/bsp/gene_lists.asp, Agilent Human Genome, Whole—Four-Plex G4112F, Feb. 7, 2007 014850, 44K (Year: 2007).*
Gene Cards ATL2 gene aliases for ATL2 gene, last accessed Nov. 27, 2017. (Year: 2017).*
Walgren et al., (J Clin Oncol. Oct. 10, 2005;23(29):7342-9. Epub Sep. 6, 2005. Review). (Year: 2005).*
Tibshirani et al., (PNAS. May 14, 2002:99(10);6567-6572). (Year: 2002).*
Kolacinska et al., Gene expression and pathologic response to neoadjuvant chemotherapy in breast cancer, Mol Biol Rep. Jul. 2012; 39(7):7435-41. doi: 10.1007/s11033-012-1576-1. Epub Feb. 9, 2012.*
Padua et al, "Roles of TGFB in Metastasis", Cell Research, vol. 19, No. 1, 2009, pp. 89-102.
Jain et al, "Biomarkers of Response and Resistance to Antiangiogenic Therapy", Nature Reviews Clinical Oncology, vol. 6, 2009, pp. 327-338.
Jubb, "Biomarkers to Predict the Clinical Efficacy of Bevacizumab in Cancer", Oncology, vol. 11, 2010, pp. 1172-1183.
Van Meeteren et al, "TGF-B Receptor Signaling Pathways in Angiogenesis; Emerging Targets for Anti-Angiogenesis Therapy", Current Pharmaceutical Biotechnology, vol. 12, No. 12, 2011, pp. 2108-2120.
Pectasides et al, "Xeliri-Bevacizumab Versus Folfiri-Bevacizumab as First-Line Treatment in Patients With Metastatic Colorectal Cancer: A Hellenic Cooperative Oncology Group Phase III Trial With Collateral Biomarker Analysis", MBC Cancer, vol. 12:271, 2012, pp. 1-10.
Varadan et al, "Abstract 4566: RNA-SEQ Identifies a TGF-B Signature That Predicts Response to Preoperative Bevacizumab in Breast Cancer", Cancer Research, vol. 73, Issue 8, Supplement 1, 2013, 1 Page.
Varadan et al, "RNA-SEQ Identifies Unique Transcriptomic Changes After Brief Exposure to Preoperative NAB-Paclitaxel (N), Bevacizumab (B) or Trastuzumab (T) and Reveals Down-Regulation of TGF-B Signaling Associated With Response to Bevacizumab", Cancer Research, vol. 72, Issue 24, Supplement 3, 2012, 1 Pages.
Lopez-Vega et al, "Activation of Angiogenic Pathway in the Prediction of Pathologic Response to Bevacizumab-Based Neoadjuvant Therapy in Breast Cancer", American Society of Clinical Oncology, www.asco.org; 2012 ASCO Annual Meeting, 3 Pages.
Lopez-Vega et al, Integrative and Multidisciplinary Clinical Trial Using Imaging, Molecular, and Dynamic Biomarkers to Predict Bevacizumab Plus Chemotherapy Response in Breast Cancer, American Society of Clinical Oncology, www.asco.org, 2011 ASCO Annual Meeting, 3 Pages.
Denkert et al, "Prediction of Response to Neoadjuvant Chemotherapy: New Biomarker Approaches and Concepts", Breast Care, vol. 6, 2011, pp. 265-272.
Thuerigen, et al., "Gene Expression Signature Predicting Pathologic Complete Response With Gemcitabine, Epirubicin, and Docetaxel in Primary Breast Cancer", Journal of Clinical Oncology, vol. 24, No. 12, Apr. 20, 2006, pp. 1839-1845.

* cited by examiner

PREDICTIVE OUTCOME ASSESSMENT FOR CHEMOTHERAPY WITH NEOADJUVANT BEVACIZUMAB

CROSS-REFERENCE TO PRIOR APPLICATIONS

This application is the U.S. National Phase application under 35 U.S.C. § 371 of International Application No. PCT/IB2013/060326, filed on Nov. 22, 2013, which claims the benefit of U.S. Provisional Patent Application No. 61/732,472, filed on Dec. 3, 2012. These applications are hereby incorporated by reference herein.

The following relates to the medical arts, oncology arts, and related arts.

In an aggressive cancer such as breast cancer, timely treatment greatly enhances the likelihood of a successful outcome, and multiple therapies are applied concurrently. In the case of breast cancer, the suspicious breast lesion is biopsied and determined to be malignant, and the cancer is typed. Neoadjuvant therapy including administration of a biologic agent such as bevacizumab (indicated for HER2 negative patients) or trastuzumab (indicated for HER2 positive patients) is administered in combination with chemotherapy for several weeks, followed by surgical removal of the lesion. A pathological complete response (pCR), in which no malignant tumor tissue or metastasis is detected in the patient, is the desired outcome. In practice, whether pCR is achieved in a given patient is not determined until after the surgery and subsequent examination of the excised tumor. If the therapy is ultimately not effective, then valuable time has been lost, and the likelihood of an ultimately successful outcome has diminished.

In view of this, various assessments are typically performed during the therapy in order to assess likely effectiveness. The tumor may be monitored by a series of imaging sessions performed over the course of the therapy using magnetic resonance (MR) imaging or another suitable imaging technique. A functional imaging modality such as positron emission tomography (PET) or single photon emission computed tomography (SPECT) may be applied to assess functional aspects, e.g. angiogenesis. Additional biopsies may be performed over the course of the treatment regimen to periodically assess the tumor.

While these approaches are useful, they have some drawbacks. Medical imaging is expensive, involves various interpretive inferences, and can be stressful for the patient. Biopsies are invasive. The patient's general health and immune system weaken as the chemotherapy regimen progresses, and so the potential for introducing infection during biopsy increases over time, as does the potential for adverse patient response to any such infection. These techniques also usually do not provide a meaningful assessment until a substantial way through the course of treatment, and the results can be unclear, especially during the early stages of treatment. For example, medical images may indicate that the tumor is not shrinking as expected; but the treatment may nonetheless ultimately achieve pCR. If evidence accumulating over time increasingly suggests that the treatment will not effective, the patient's physician must make the difficult choice of continuing with a therapy regimen that may not work, or alternatively terminating or adjusting the therapy without knowing whether it would ultimately have been successful.

The use of genetic tests has been contemplated for correlating patient therapy response with expression of specific genes or microRNAs (miRNA) measured using gene arrays, immunohistochemistry, or reverse transcription-polymerase chain reaction (RT-PCR). Typically, these molecular markers are measured at baseline before the patient undergoes neoadjuvant therapy and these baseline measurements are used to stratify patients into groups that may or may not benefit from subsequent therapy. However, these predictors from baseline breast biopsies have not achieved sufficient specificity to be routinely used in the clinic. In contrast, the brief-exposure neoadjuvant paradigm involves taking patient breast biopsies at baseline (before therapy) and a few days after a single dose of neoadjuvant therapy. Molecular profiles are then conducted on the two patient biopsies and changes in the profiles between these two biopsies are used to predict eventual benefit from the full course of neoadjuvant treatment.

The following contemplates improved apparatuses and methods that overcome the aforementioned limitations and others.

According to one aspect, a method comprises: generating differential gene expression level information for an input set of genes, the differential gene expression level information comparing: (i) baseline gene expression level information from a baseline sample of a breast tumor of a patient acquired before initiating a breast cancer therapy regimen to the patient and (ii) response gene expression level information from a response sample of the breast tumor acquired after initiating the breast cancer therapy regimen by administering a first dose of bevacizumab to the patient; and computing a pathological complete response (pCR) prediction for the patient based on the differential gene expression level information for the input set of genes. The generating and computing are suitably performed by an electronic data processing device.

According to another aspect, a method comprises: initiating a breast cancer therapy regimen comprising at least bevacizumab by administering a first dose of bevacizumab to a patient; before the initiating, acquiring a baseline sample of a breast tumor of the patient; after the initiating, acquiring a response sample of the breast tumor of the patient; generating baseline and response gene expression level information from the baseline and response samples, respectively, for an input set of genes; generating differential gene expression level information comparing the baseline and response gene expression level information for the input set of genes; and computing a pathological complete response (pCR) prediction for the patient based on the differential gene expression level information for the input set of genes.

According to another aspect, in a method as set forth in one of the two immediately preceding paragraphs employs an input set of genes belonging to the transforming growth factor β (TGF-β) signaling pathway. According to another aspect, in a method as set forth in one of the two immediately preceding paragraphs employs an input set of genes including at least two genes of the group consisting of CDKN2B, ATL2, CTGF, INHBA, ID4, BMPR1A, CD1E, TFDP1, AMIGO2, DDIT4, TGFB2, SPP1, CD28, PMEPA1, FAT4, KDM6B, MAP3K4, FAM162A, MYH11, and PPP2R1B. Other suitable choices for the input set of genes are also disclosed herein, including an illustrative example in which the input set of genes includes 61 genes.

According to another aspect, a method comprises, for each study subject of a population of study subjects: initiating an oncological therapy regimen including at least a neoadjuvant therapeutic agent by administering a first dose of the neoadjuvant therapeutic agent to the study subject; before the initiating, acquiring a baseline sample of a malignant tumor in the study subject; after the initiating, acquiring a response sample of the malignant tumor in the study subject; after acquiring the response sample, completing the oncological therapy regimen for the study subject; after completing the oncological therapy regimen, determining pathological complete response (pCR) status of the study subject; processing the baseline and response samples to generate baseline gene expression level information and response gene expression level information respectively for at least 1000 genes; and calculating differential gene expression level information for the study subject comparing the baseline gene expression level information and the response gene expression level information. A classifier is then trained using the differential gene expression level information calculated for the study subjects of the population as training data to generate a trained classifier that outputs a pCR prediction computed based on received differential gene expression level information for an input set of genes.

According to another aspect, a method utilizes the trained classifier generated by the method of the immediately preceding paragraph. The method comprises, for a patient undergoing clinical treatment: initiating the oncological therapy regimen by administering a first dose of the neoadjuvant therapeutic agent to the patient; before the initiating, acquiring a baseline patient sample of a malignant tumor in the patient; after the initiating, acquiring a response patient sample of the malignant tumor in the patient; generating patient differential gene expression level information for the input set of genes based on the baseline and response patient samples; and generating a pCR prediction for the patient by inputting the patient differential gene expression level information to the trained classifier, the generating being performed prior to completing the oncological therapy regimen on the patient.

One advantage resides in providing an early indication of whether neoadjuvant bevacizumab therapy in conjunction with chemotherapy is likely to achieve a pathological complete response (pCR) for breast cancer.

Another advantage resides in providing a development methodology for developing a genetic test to determine whether a neoadjuvant therapy is likely to achieve pCR.

Numerous additional advantages and benefits will become apparent to those of ordinary skill in the art upon reading the following detailed description.

The invention may take form in various components and arrangements of components, and in various process operations and arrangements of process operations. The drawings are only for the purpose of illustrating preferred embodiments and are not to be construed as limiting the invention.

FIGS. 7A, 7B, and 7C show a 61-gene signature developed herein with the genes ordered according to their level of contribution to the signature Disclosed herein are predictive outcome assessment tests for determining likelihood that a breast cancer therapy including chemotherapy with neoadjuvant bevacizumab will produce a pathological complete response (pCR) in a given patient. Ribonucleic acid (RNA) sequencing is performed on tumor biopsies taken at two time points from a given patient a first biopsy taken at time of diagnosis, and a second biopsy taken after administration of a single dose of preoperative bevacizumab (e.g., 10-14 days after). The molecular profiles of the two biopsies are compared to examine differential gene expression levels for genes associated with TGF-beta (i.e., TGF-β) activity. Some suitable gene signatures disclosed herein were developed based on prior biological evidence of their association with breast cancer metastases and TGF-beta activity. Using these genes, a nearest centroid-based classifier (or other classifier) is trained that assigns a pCR prediction indicating the likelihood of an individual patient achieving pCR using the signature genes associated with TGF-beta activity. As used herein, a gene refers to a human gene and not to any nonhuman genes, and similarly ribonucleic acid (RNA) refers to human RNA, proteins refer to human proteins, and so forth, and not to any nonhuman RNA, proteins, or so forth.

Also disclosed herein are test development techniques that produce robust outcome-predictive classifiers.

Figure 1:
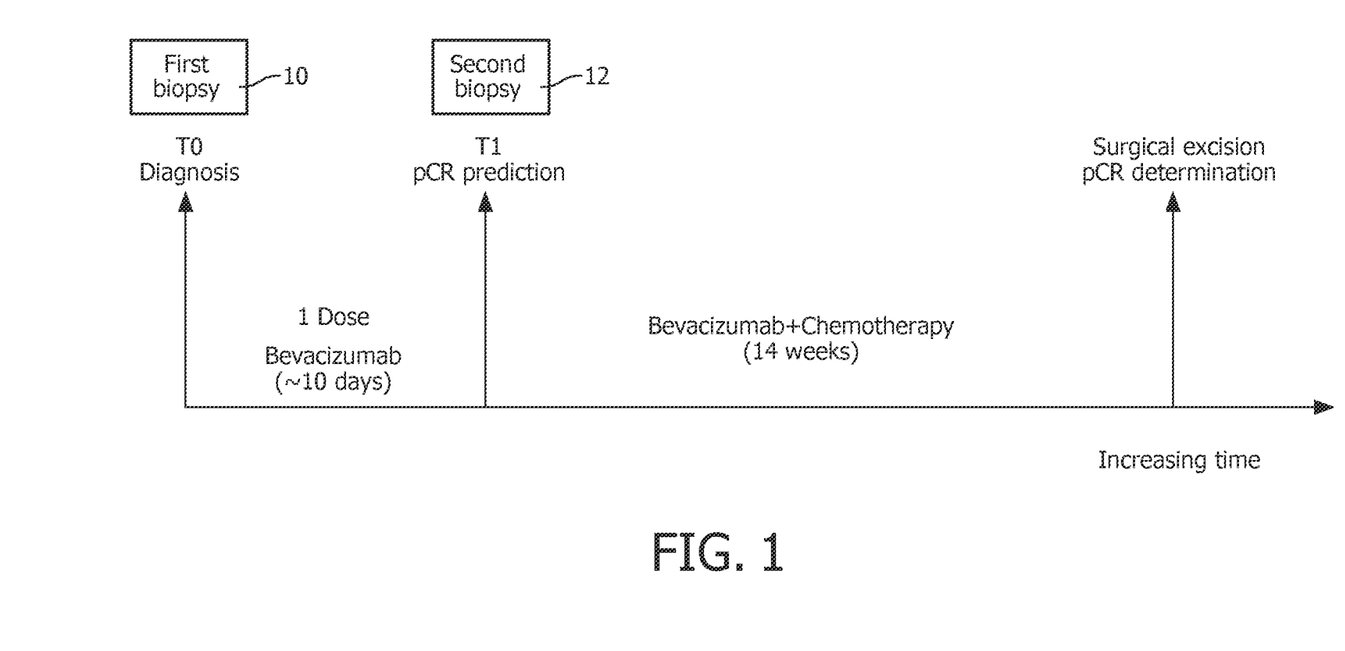
FIG. 1 diagrammatically shows an illustrative breast cancer treatment regimen including chemotherapy with neoadjuvant bevacizumab followed by surgical excision of the breast tumor.
Figure 2:
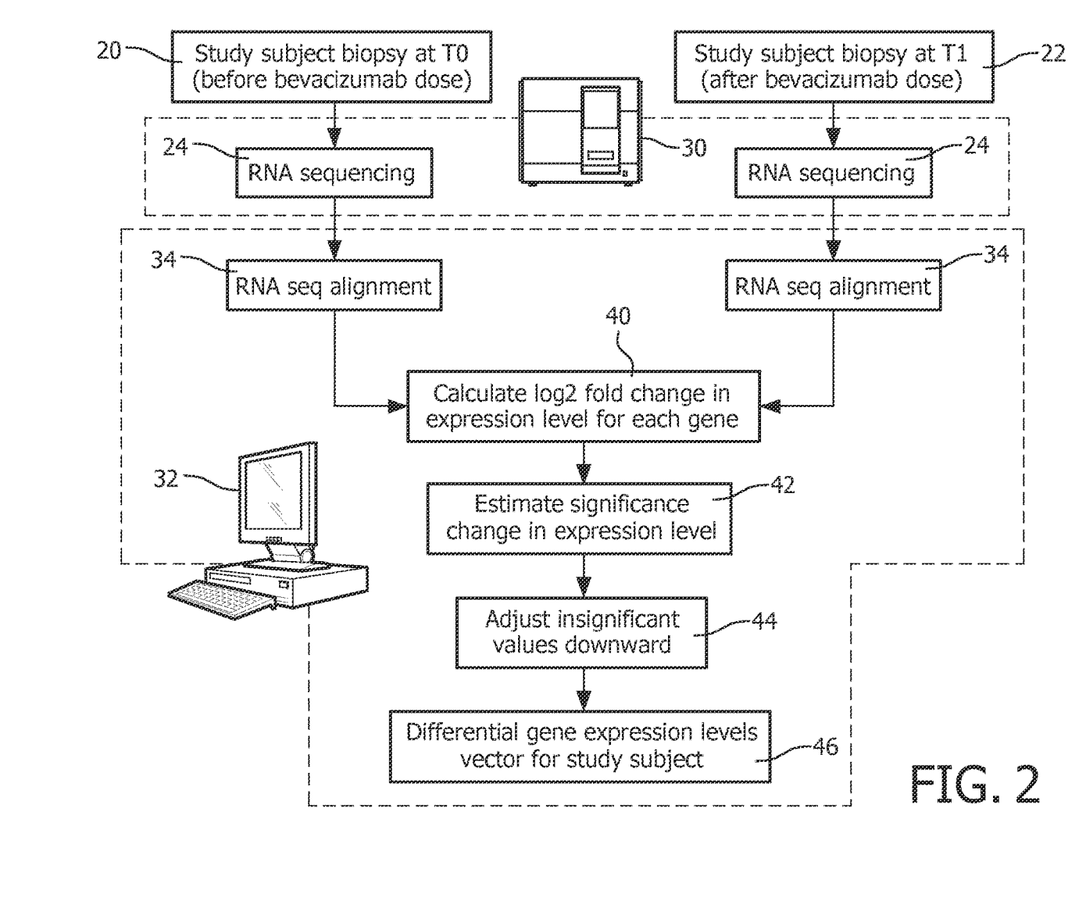
FIGS. 2 and 3 diagrammatically show development of a predictive outcome assessment test for the breast cancer therapy of FIG. 1, with FIG. 2 showing processing performed on each study subject of a study population and FIG. 3 showing processing performed on the aggregate study population to generate a predictive classifier.

With reference to FIG. 1, the illustrative breast cancer therapy regimen is described. At a time T0, the patient is diagnosed with breast cancer, and a first biopsy is performed to extract a first biopsy sample 10 from the breast lesion of the patient to establish a baseline. The first biopsy sample 10 is analyzed to type the breast cancer. In the patient whose treatment is diagrammatically shown in FIG. 1, the breast cancer is identified as HER2 negative. HER2 is Human Epidermal Growth Factor Receptor 2, also known as Neu, ErbB-2, CD340 (cluster of differentiation 340) or p185. It is a protein that that is encoded by the ERBB2 gene. For this type of breast cancer, an oncological therapy regimen including chemotherapy with neoadjuvant bevacizumab may be prescribed however, it does not always produce satisfactory results. The illustrative breast cancer therapy regimen of FIG. 1 includes chemotherapy with neoadjuvant bevacizumab. In the therapy regimen shown in FIG. 1, this initial dose of bevacizumab is not accompanied with any other therapy but in other situations it may be accompanied with additional chemotherapy as well. At a time T1 occurring after the initial dose of bevacizumab is administered and before the first dose of combination bevacizumab+chemotherapy, a second biopsy is performed to extract a second biopsy sample 12 from the breast lesion. The disclosed pCR prediction test is performed based on differential gene expression level information extracted from the first and second biopsies, using a suitable signature as disclosed herein. The pCR prediction test generates a pCR prediction indicative of likelihood that the therapy regimen will achieve pathologic complete response (pCR) in the patient. Note that the pCR prediction is diagrammatically shown in FIG. 1 at time T1; however, it is to be understood that the pCR prediction is generated some time after the second biopsy is performed, since computation of the pCR prediction relies upon data obtained from the second biopsy sample 12. However, it is preferable that the pCR prediction is generated before the combination bevacizumab+chemotherapy is administered—in that way, the physician can take into account the pCR prediction in deciding whether to go forward with the therapy regimen shown in FIG. 1. In some embodiments there is a three week (21 day) interval between the first bevacizumab dose and the start of combination therapy, and the second biopsy procedure is performed about 10-14 days after the first bevacizumab dose, leaving at least one week to analyze the first and second biopsy samples 10, 12 and generate the pCR prediction. In our study, all the patients received combination therapy subsequence to the second biopsy and at the end of this regimen, the breast tumor was surgically removed (i.e. excised), and the surgical examination and optionally other tests enable medical personnel to determine whether the patient has achieved the desired pathological complete response (pCR), in which no malignant tumor tissue or metastasis is detected in the patient. The predictive signature was developed in our study using the pCR status of the patients as calculated at the end of the combination regimen Starting with FIG. 2, an approach is described for developing a predictive outcome assessment for determining whether an oncological treatment regimen including an adjuvant therapy agent is likely to be successful. In the illustrative example, this approach was used to develop the disclosed predictive test for efficacy of neoadjuvant bevacizumab in conjunction with chemotherapy for breast cancer patients with HER2-negative breast cancer. However, the disclosed approach is more generally applicable to any neoadjuvant therapy. The processing diagrammatically depicted in FIG. 2 is performed for each study subject of a population of study subjects. For a given study subject, the input are a first biopsy 20 and a second biopsy 22. The first biopsy 20 is equivalent to the first biopsy 10 shown in FIG. 1, but is performed on a study subject rather than on a clinical patient. The second biopsy 22 is equivalent to the second biopsy 12 shown in FIG. 1, but again is performed on the study subject rather than on a clinical patient. The first biopsy sample 20 is processed by performing ribonucleic acid (RNA) sequencing 24, and the second biopsy sample 22 is also processed by performing the same RNA-sequencing 24. The RNA sequencing 24 can employ any suitable RNA sequencing apparatus 30, such as an illustrative Illumina® Genome Analyzer IIx.

The output of the RNA sequencing operations 24 are messenger RNA (mRNA) levels in the respective biopsy samples 20, 22 for various mRNA strands. As this is electronic data, thereafter processing is suitably performed by a computer 32 (although a separate computer 32 is illustrated, some or all computer operations may optionally be performed by a computer component, e.g. microprocessor and associated electronic memory, et cetera, of the RNA sequencing apparatus 30). The RNA strands of the first and second biopsy samples 20, 22 are aligned in respective alignment operations 34. In a suitable approach, the RNA sequencing strands (i.e. RNA-seq data) are aligned with a standard human RefSeq (see ncbi.nlm.nih.gov/RefSeq/) using the TopHat spliced read mapper (see tophat.cbcb.umd.edu/, last accessed Nov. 13, 2012) followed by Cufflinks (see cufflinks.cbcb.umd.edu/, last accessed Nov. 28, 2012) to calculate the gene expression levels. The output of the alignment operation 34 applied to the RNA sequencing data of the baseline biopsy sample 20 is baseline gene expression level information in the form of RNA levels, and the output of the alignment operation 34 applied to the RNA sequencing data of the response biopsy sample 22 is response gene expression level information in the form of RNA levels. It is to be appreciated that the RNA levels can be measured by alternative systems, such as using a microarray. The disclosed test development approach is empirical (although pathway-based enrichment is contemplated and described herein), and so the gene expression level information preferably includes data for at least 1000 genes, and more preferably at least 10,000 genes. By way of illustrative example, the Illumina® Genome Analyzer IIx provides gene expression level information for 35767 genes (in the form of mRNA transcripts). As another example, the GeneChip® Human Gene ST 1.0 (available from Affimetrix Inc., Santa Clara, Calif., USA) provides 36,079 transcripts.

With continuing reference to FIG. 1, in an operation 40, differential gene expression level information are calculated for the study subject. The differential gene expression level information compare the baseline gene expression level information and the response gene expression level information. In a suitable approach, the differential expression level for each gene of the study subject is calculated as a log-fold change between the baseline gene expression level and the response gene expression level. Because the noise level for RNA levels varies widely between genes, a normalization is suitably applied. In the illustrative example, the RNA levels are assumed to follow a Poisson distribution, which in an operation 42 is used to estimate the significance of the differential gene expression levels. In an operation 44, genes whose differential expression level is deemed insignificant based on operation 42 are optionally adjusted downward, for example by dividing the differential expression level by a factor of 10 or 100, so as to mathematically limit their effect in subsequent processing. (In an alternative approach, insignificant differential levels can be set to zero; however, this can complicate subsequent mathematical processing if it leads to division by zero, for example. As another alternative, the adjustment operations 42, 44 can be omitted; however, this can introduce some noise.) The final output, for each study subject, is differential gene expression level information, suitably represented in the illustrative example by a differential gene expression levels vector 46 for the subject. In this vector 46, each vector element corresponds to a gene and its value is the differential RNA level for that gene (optionally adjusted as per operations 42, 44). In the illustrative example in which there are 35,767 measured genes, the vector 46 has 35,767 elements.

The processing of FIG. 2 is applied for each study subject of the population, so as to generate a set of differential gene expression levels vector 46 for the subjects. This differential gene expression information is then used to train a classifier.

Figure 3:
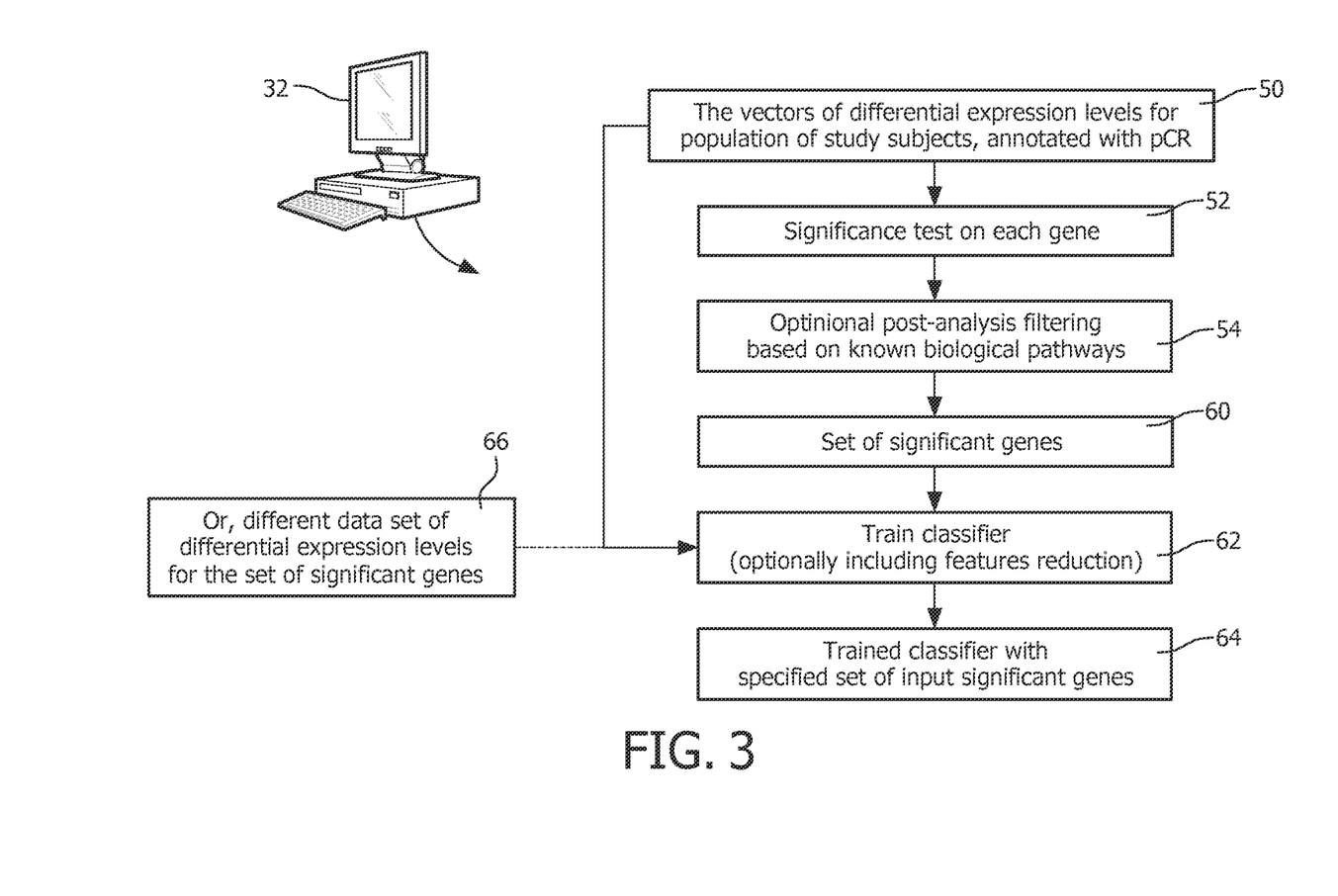

With reference to FIG. 3, the set of differential gene expression levels vectors 46 for the subjects of the population of study subjects forms a data set 50. In this data set, each study subject is annotated with pCR status. This status is known for the study subjects because each study subject goes through the chemotherapy regimen of FIG. 1, and at the end of this regimen the study subject undergoes surgical excision of the breast tumor and staging to determine whether the study subject has achieved pCR. Thus, the data set 50 is an annotated data set suitable for training a classifier designed to classify a new patient as to whether the treatment regimen would achieve pCR in the new patient. Before training the classifier, however, it may be useful to select a set of significant genes for input to the classifier, rather than training the classifier on all genes for which differential gene expression data are available, which can be computationally difficult or even prohibitive. Moreover, if the classifier operates on a relatively small sub-set of the available genes, then only those genes need to be measured in order to classify the new patient. Accordingly, in an operation 52, the significance of each gene for predicting pCR is analyzed. In a suitable approach, a Mann-Whitney significance test (also known as the Wilcoxon rank-sum test) is applied, although other significance tests such as a student-t test could alternatively be used. In a typical significance test, a null hypothesis is assumed, in this case that the differential mRNA level for gene under test is not discriminative for pCR, and the Mann-Whitley test is performed to generate a p-value indicative of the probability that the pCR status values of the study subjects would have the distribution exhibited in the population if this null hypothesis was actually true. A lower value of the p-value indicates lower likelihood of observing the distribution in population in the absence of correlation; thus, a lower p-value is more suggestive of statistical significance. In one approach, the significant genes can be chosen using a significance level threshold a, where p<α is considered statistically significant. Typically a threshold of α=0.05 or α=0.01 is used, although other thresholds can be employed, or alternatively a "top-N" genes with lowest p-value can be selected.

In an optional filtering operation 54, the significant genes can be filtered based on enrichment information such as known signaling pathways, for example as compiled in the KEGG pathway database. See genomejp/kegg/pathway.html, last accessed Nov. 13, 2012. For example, if many of the statistically significant genes (as indicated by the testing 52) belong to a single pathway, then optionally the filtering 54 may eliminate any statistically significant genes that do not belong to that pathway. Alternatively, the pathway information may be used to add additional significant genes by adding genes of the pathway with p-value close to, but greater than, the selection threshold a. Other enrichment methodologies are also contemplated. Note that while the enrichment operation 54 is shown in FIG. 3 as being performed (along with the other operations diagrammatically shown in FIG. 3) by the computer 32, it is contemplated for the enrichment operation 54 to be performed manually, e.g. by having a person with suitable medical training compare the significant genes output by the significance test 52 with a pathways database.

With continuing reference to FIG. 3, the output of significance testing operation 52 and optional enrichment operation 54 is a set of significant genes 60. In an operation 62, a classifier is trained. The classifier to be trained is designed to receive differential gene expression level information of a patient for the set of significant genes 60 and to output a pCR prediction computed based on the received patient differential gene expression level information. The classifier is trained using the pCR status-annotated set of differential gene expression level information 50 for the significant genes as training data. In the illustrative example, the differential gene expression levels vectors 46 for the study subjects have 35,767 genes (in the form of mRNA transcripts). If (again as an illustrative example) there are 100 significant genes to be used in the classifier, then only the 100 vector elements corresponding to those 100 significant genes are used as the training data. The classifier can be substantially any type of binary classifier, and can be designed to input either a probability (i.e. a soft binary classifier indicating a likelihood that the patient will achieve pCR via the treatment) or a binary answer (i.e. a hard binary classifier). In illustrative examples herein, a shrunken centroid classifier is employed, which performs gene selection during the training that removes genes from the initial input set of genes. The output of the classifier training operation 62 is the trained classifier 64.

The pCR status-annotated set of differential gene expression level information 50 is used as the training data. In this case, the resulting classifier 64 is designed to receive as input differential gene expression level data of the type and format of the differential gene expression levels vectors 46 for the study subjects. In the illustrative example, these data are in the form of mRNA transcripts generated by RNA sequencing.

However, in an alternative approach, the classifier can be trained to employ input differential gene expression level data for the set of significant genes in another type or format, such as data generated by reverse transcription-polymerase chain reaction (RT-PCR) processing, microarray processing to generate protein level data, or so forth. To do this, a training differential gene expression data set 66 of the desired type/format is provided. The data set 66 is preferably also for the population of study subjects and is annotated with study subject pCR status, but is acquired using a different technique, e.g. RT-PCR or microarray analysis. In this alternative approach, the differential gene expression data set 66 for the significant genes 60 serves as input to the classifier training operation 62, and the resulting trained classifier 64 is designed to receive input differential gene expression data in the format of the data set 66. This alternative approach allows a "whole genome" technique such as RNA sequencing (as per FIG. 2) to be used to generate a reasonably comprehensive gene expression data set (i.e., the differential gene expression levels vectors 46 for the study subjects) that is used to identify the significant genes 60, thus ensuring that a comprehensive search for the most significant genes is performed. But, the resulting test is embodied by the trained classifier 66, in this alternative embodiment uses a patient differential gene expression data set generated by another technique such as RT-PCR or microarray analysis. This other technique may advantageously be less costly, more readily available, targeted to the identified significant genes, or otherwise have advantages for clinical testing over the RNA sequencing or other comprehensive technique used in the significant genes identification.

Figure 4:
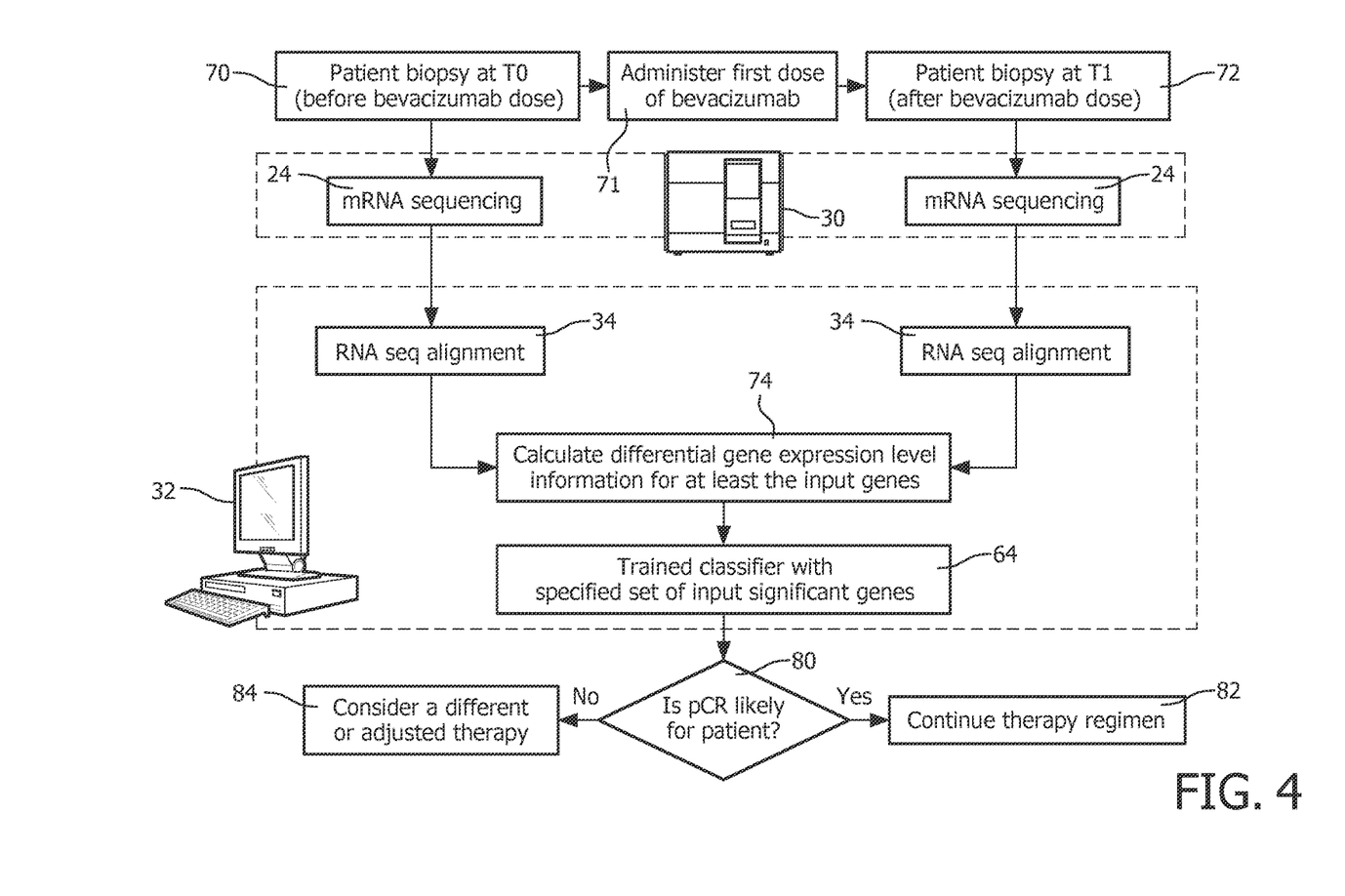
FIGS. 4 and 5 diagrammatically show two alternative embodiments of the application of the predictive outcome assessment test as developed in FIGS. 2 and 3 to predict pCR outcome of a clinical patient.

With reference to FIG. 4, application of the trained classifier 64 as a predictive outcome assessment test is described. A patient who has been diagnosed with HER2 negative breast cancer and prescribed the treatment regimen of FIG. 1 (in this illustrative example) is initially biopsied to generate a baseline patient biopsy 70 corresponding to the baseline biopsy sample 20 of the study subject. The patient in the context of FIG. 4 is typically a new patient, and not a member of the population of study subjects analyzed in the operations of FIGS. 2 and 3. After the initial biopsy, the patient receives the first dose of bevacizumab 71, typically without any concomitant chemotherapy agent being administered, although it is contemplated to also have some administered chemotherapy agent as shown in the illustrative regimen of FIG. 1. Thereafter, e.g. in 10-14 days, the patient undergoes a second biopsy to generate a response patient biopsy 72 corresponding to the response biopsy sample 22 of the study subject. This now leaves a week or longer for the biopsy analysis set forth in the remainder of FIG. 4 to be performed in order to generate a pCR prediction for consideration by the patient's physician. In illustrative FIG. 4, the same RNA sequencing apparatus 30 as was used for processing study subject biopsy samples (see FIG. 2) is again shown; however, it is to be understood that an equivalent RNA sequencing apparatus can be used e.g., the same apparatus model but not the specific same instrument, or an instrument of a different model that generates substantially the same RNA reads.

In the example of FIG. 4, the classifier 64 is assumed to have been trained using the differential gene expression levels vectors 46 generated by RNA sequencing as per FIG. 2. Accordingly, the baseline and response biopsy samples 70, 72 of the patient are processed by the same RNA sequencing and alignment operations 24, 34 as already described for the study subjects (see FIG. 2) to generate baseline and response patient RNA level information. This RNA level information is in an operation 74 to perform processing equivalent to the operations 40, 42, 44 of FIG. 2, but with the difference that the operation 74 is optionally (but not necessarily) limited to the RNA level information for the significant genes that serve as input to the trained classifier 64. The differential gene expression level information output by the operation 74 is in the form of differential RNA level information, and is input to the trained classifier 64 to generate a pCR prediction for the patient. The operations 34, 74 are indicated as being performed by the same computer 32 as was used in the training processing of FIGS. 2 and 3, but again a different but analogously programmed computer can be employed. A visually perceptible representation of the pCR prediction generated by the trained classifier 64 is preferably displayed before continuing the oncological therapy regimen beyond the initial bevacizumab dose 71, for example being displayed on a video display unit as a number, or as a bar whose length indicates probability of achieving pCR in the patient, or as a printout on a piece of paper, or so forth.

With continuing reference to FIG. 4, in a decision 80 the patient's physician considers whether the patient is likely to achieve pCR status by employing the therapy regimen subsequent to the initial bevacizumab dose 71. In making this decision, the physician suitably considers the pCR prediction calculated by the trained classifier 64 based on the input patient differential RNA level information. However, the physician may consider additional factors in making the decision 80, such as other tests performed on the patient, the doctor's medical expertise, the likelihood of achieving a result that is less optimal than pCR but possibly still a beneficial result for the patient, or so forth. The decision 80 is typically made in consultation with the patient. If the physician decides that the regimen is likely to achieve pCR status for the patient, then the therapy regimen is continued in an operation 82. On the other hand, if the physician decides that the regimen is not likely to achieve pCR status for the patient, then the therapy is suitably modified, or a different therapy is applied, in an operation 84.

Figure 5:
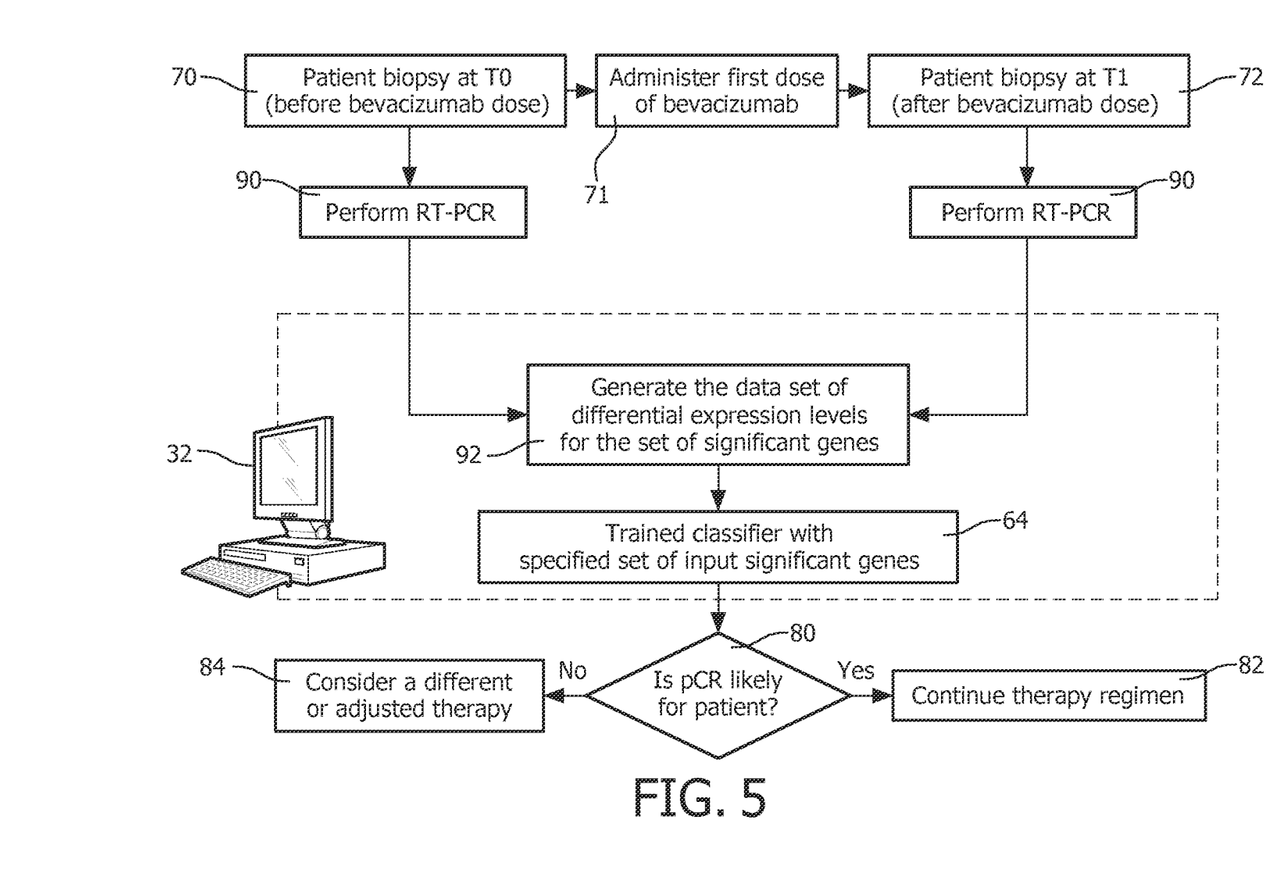

With reference to FIG. 5, application of the trained classifier 64 as a predictive outcome assessment test is described in an alternative case in which the classifier training operation 62 of FIG. 2 employed the alternative data set of differential gene expression level data 66, namely a data set generated by RT-PCR in the illustrative example of FIG. 5. In embodiment of FIG. 5, the patient biopsy samples 70, 72 are acquired before and after the initial bevacizumab dose 71, as already described with reference to FIG. 4. The biopsy samples 70, 72 are processed by RT-PCR 90 and the resulting baseline and response gene expression level data are processed in an operation 92 to generate differential gene expression level data for the input genes in the same format as that of the (alternative) training data set 66 of FIG. 3. The differential gene expression level information output by the operation 92 is in the same form as that of the training data set 66, and is input to the trained classifier 64 (which, in this embodiment, was trained using the training data set 66) to generate a pCR prediction for the patient. The decision operation 80 and the subsequent treatment options 82, 84 are as already described with reference to FIG. 4.

With reference to FIGS. 2 and 3, embodiments have been described of development methods and systems for developing a predictive outcome assessment test for predicting whether a pCR outcome is likely for a patient receiving an oncological therapy regimen including administration of a neoadjuvant therapy agent. With reference to FIGS. 4 and 5, embodiments have been described of methods and systems for applying such a predictive outcome assessment test for predicting whether a pCR outcome is likely for a given patient.

In the following, an illustrative actually performed example is described, in which a development method paralleling that described with reference to FIGS. 2 and 3 was applied to develop a predictive outcome assessment test for the breast cancer therapy regimen diagrammatically shown in FIG. 1, which includes chemotherapy (carboplatin and nab-Paclitaxel) with neoadjuvant bevacizumab. The development of the predictive outcome assessment test involved data from a clinical trial in which the breast cancer patients received a single dose of bevacizumab treatment as a brief-exposure along with two biopsies of the tumor, one taken before therapy and one taken around 10-15 days after the single dose. Transcriptomes of core biopsy RNA were sequenced from 13 pairs of breast tumors obtained from neoadjuvant clinical trials BrUOG 211A/211B. Study subjects whose breast tumors were HER2 negative were given a run-in dose of Bevacizumab, followed by combination biologic/chemotherapy Bevacizumab+carboplatin+Nab-paclitaxel. Biopsy pairs obtained pre/post 10 day exposure to run-in monotherapy were sequenced. Paired-end sequencing was done on Illumina GAII platform using amplified total RNA with 74 bp (base pair) read length, yielding expression data for 22,160 genes and 34,449 transcripts. Transcriptomic changes upon brief exposure to bevacizumab monotherapy were evaluated assuming Poisson-distributed read-counts. These operations correspond to operations 24, 34 of FIG. 2 operating on biopsy samples 20, 22.

The calculation of the differential gene expression levels vector 46 for each subject, corresponding to operations 40, 42, 44 of FIG. 2, were performed as follows. The gene expression level was taken at baseline (T0) and after brief-exposure (T1) in units of FPKM, i.e. Fragments Per Kilobase of transcript per Million mapped reads. The log 2 fold change (operation 40) was calculated as log 2(FPKM (T1)/(FPKM (T0)) values. Operation 42 was performed using Poisson-distributed reads to estimate significance of log 2 fold change (FC). Operation 44 was performed by computing significance-adjusted log 2FC by dividing non-significant ($p<0.05$) log 2FCs by 100.

The selection statistically significant genes, i.e. operation 52 of FIG. 3, was performed using the Mann-Whitney test to check for significance-adjusted log 2FC association with pCR. The enrichment analysis (operation 54 of FIG. 3) was performed to identify KEGG pathways associated with pCR. Only four pathways were found to be significantly associated with pCR after multiple testing correction. Of these four pathways, it was found that the transforming growth factor beta (TGF-beta or TGF-β) signaling pathway had 10 out of 85 genes in total associated with pCR. To further enrich the set of significant genes, the medical literature was consulted. Padua et al developed a 153 gene TGF-β response signature by exposing four human cell lines (MCF-10A, MDA-MB-213, HPL1 and HaCaT) to TGFB1 for 3 hours and capturing genes those expression levels changed significantly upon exposure. Padua, "Roles of TGFβ in metastasis", Cell Research vol. 19 pages 89-102 (2009). In view of this, the 10 significant genes belonging to the TGF-β signaling pathway that were identified by the significance testing 52 were enriched by the 153 genes related to TGF identified by Padua et al. As there was one gene overlap, this resulted in a preliminary set of 162 significant genes, which was then processed to filter out genes that have low variance in significance-adjusted log fc values (<0.01) across all samples, and to filter out genes that have low absolute significance-adjusted log fc values in more than half of samples, namely genes that have absolute log fc<0.1 in at least 7 of the 13 samples were excluded. The resulting gene list included 107 genes, corresponding to the set of significant genes 60 of FIG. 3.

Figure 6:
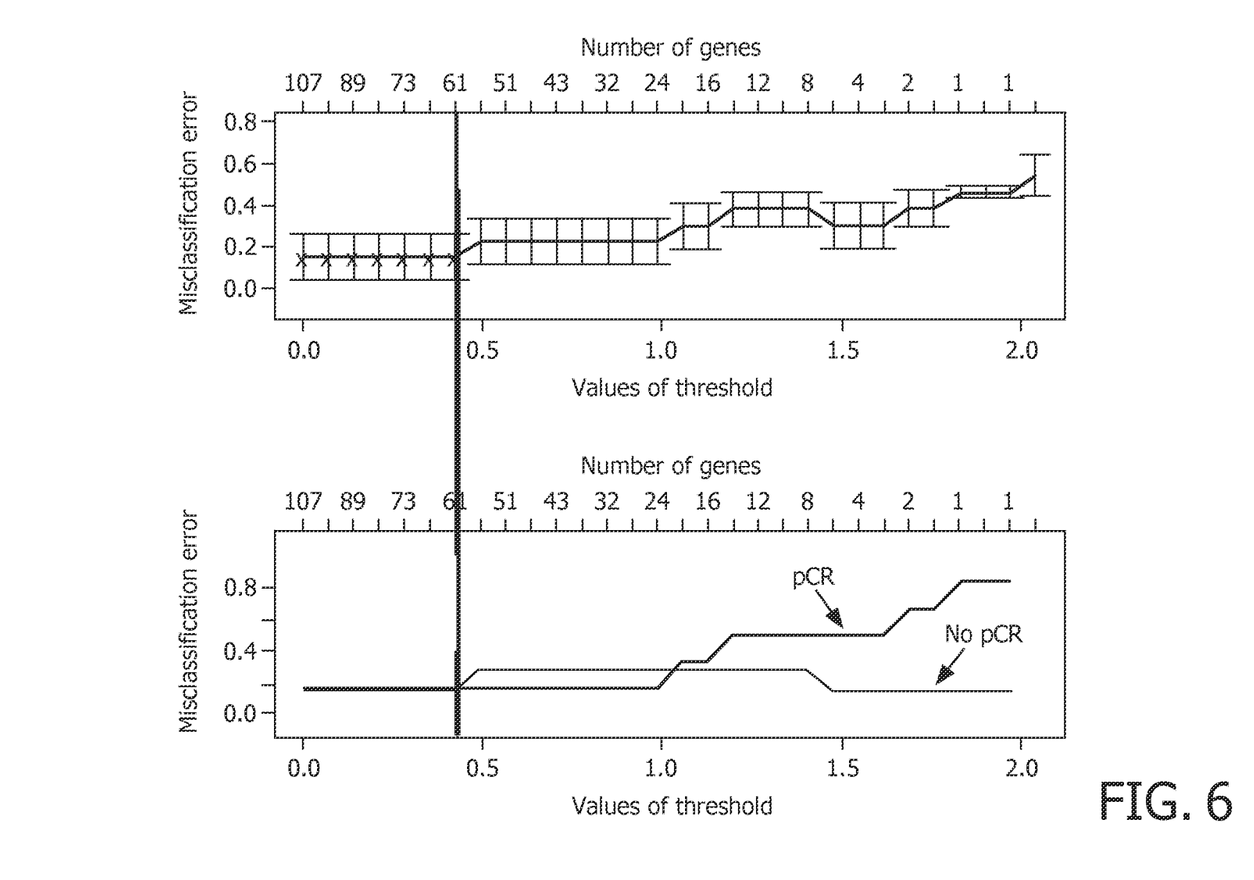
FIG. 6 diagrammatically shows misclassification error of an actually developed shrunken centroid classifier as a function of the number of input genes.

With reference to FIG. 6, the chosen classifier to distinguish between pCR and non-pCR patients was a shrunken centroid classifier, and the classifier training 62 of FIG. 3 was initiated with the 107 genes. Three-fold cross-validation was performed, that was repeated 10 times. Performance of shrunken centroid classifier was used to identify shrinkage threshold result. As seen in FIG. 6, the trained classifier begins to exhibit instability after the "shrinking" of the centroids excludes around 50 genes resulting in a 61-gene classifier. The misclassification error as shown in the upper part of FIG. 6 is calculated using a 3-fold cross-validation strategy where a subset of the patient samples are chosen to train the classifier and the remaining samples are used to test the performance of the classifier. Therefore, as the misclassification error increases with smaller and smaller number of genes being included in the signature, that is suggestive of the signature becoming less effective in predicting pCR. Therefore, it makes sense to choose at least 61 out of the 107 genes and FIGS. 7A, 7B, and 7C show the 61-gene signature with the genes ordered according to their level of contribution to the signature—the most informative gene being listed at the top.

Thus, it was found that the classifier preferably has at least 61 genes. Classifiers with fewer than 61 genes continue to be useful but experience higher likelihood of making errors in predicting pCR. It was found that the centroids of most genes associated with pCR were negative, which is suggestive of down-regulation of TGF-β activity and indicates that down-regulation of TGF-β activity upon brief exposure to bevacizumab is associated pCR.

Figure 7A:
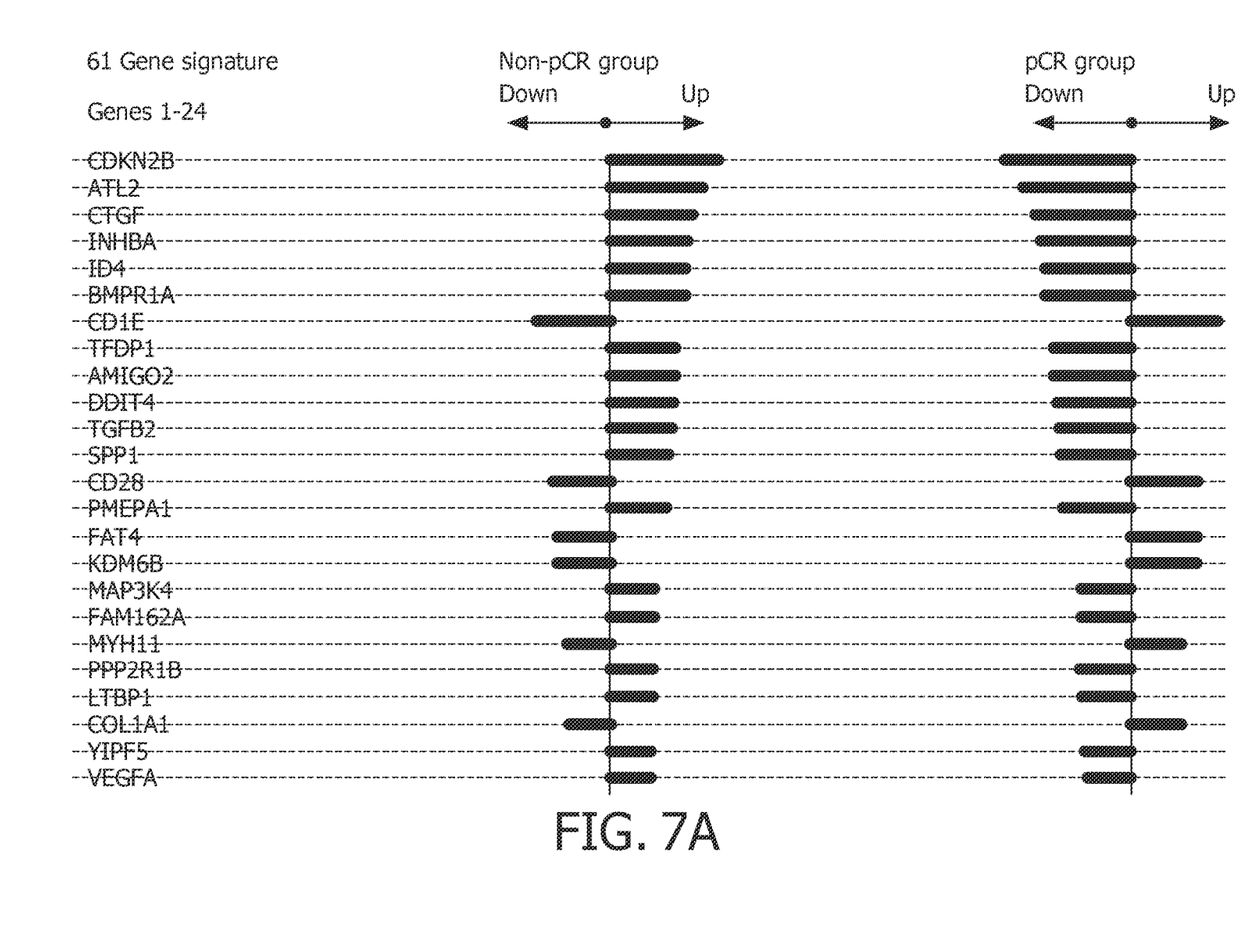
Figure 7B:
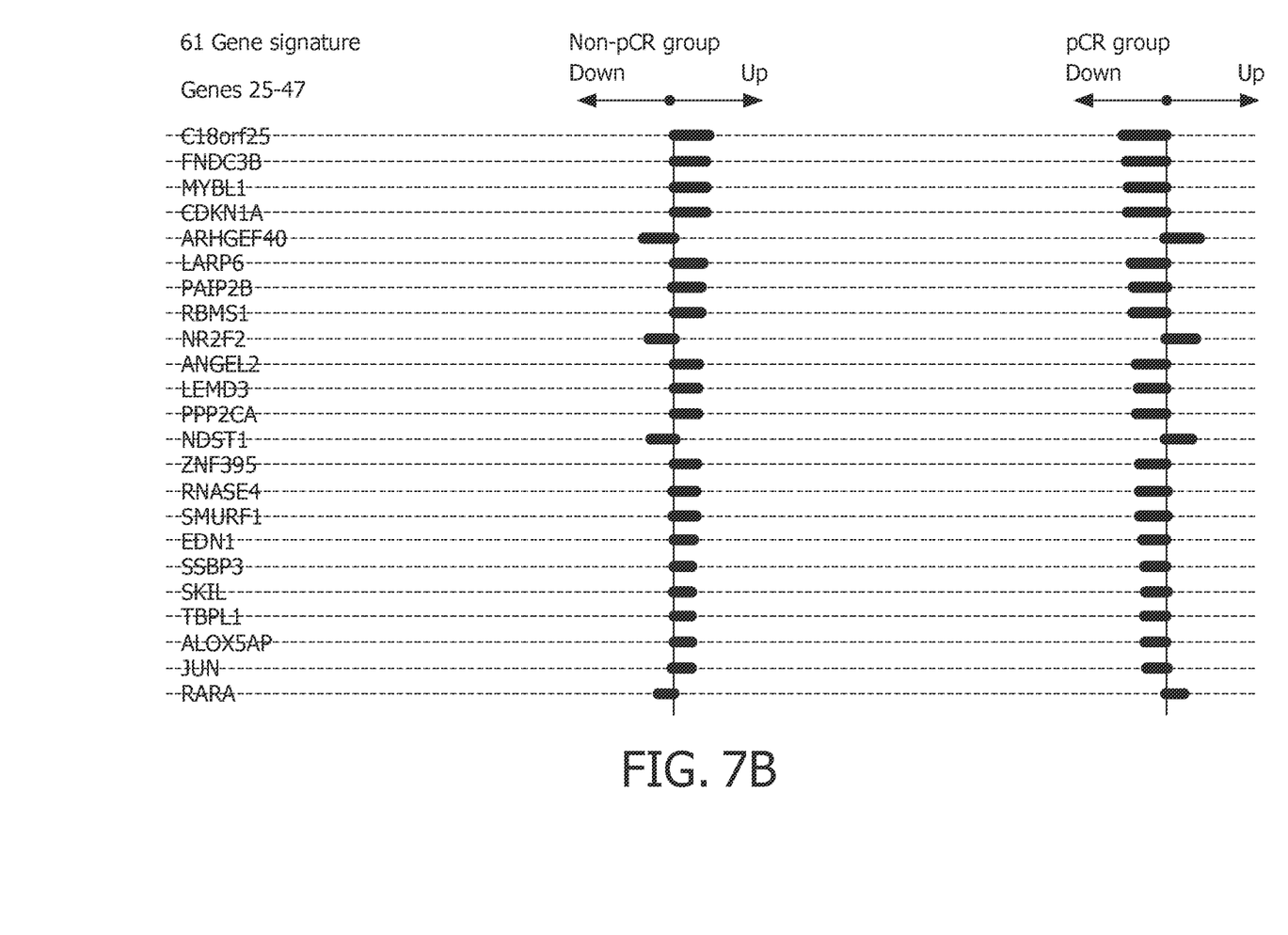
Figure 7C:
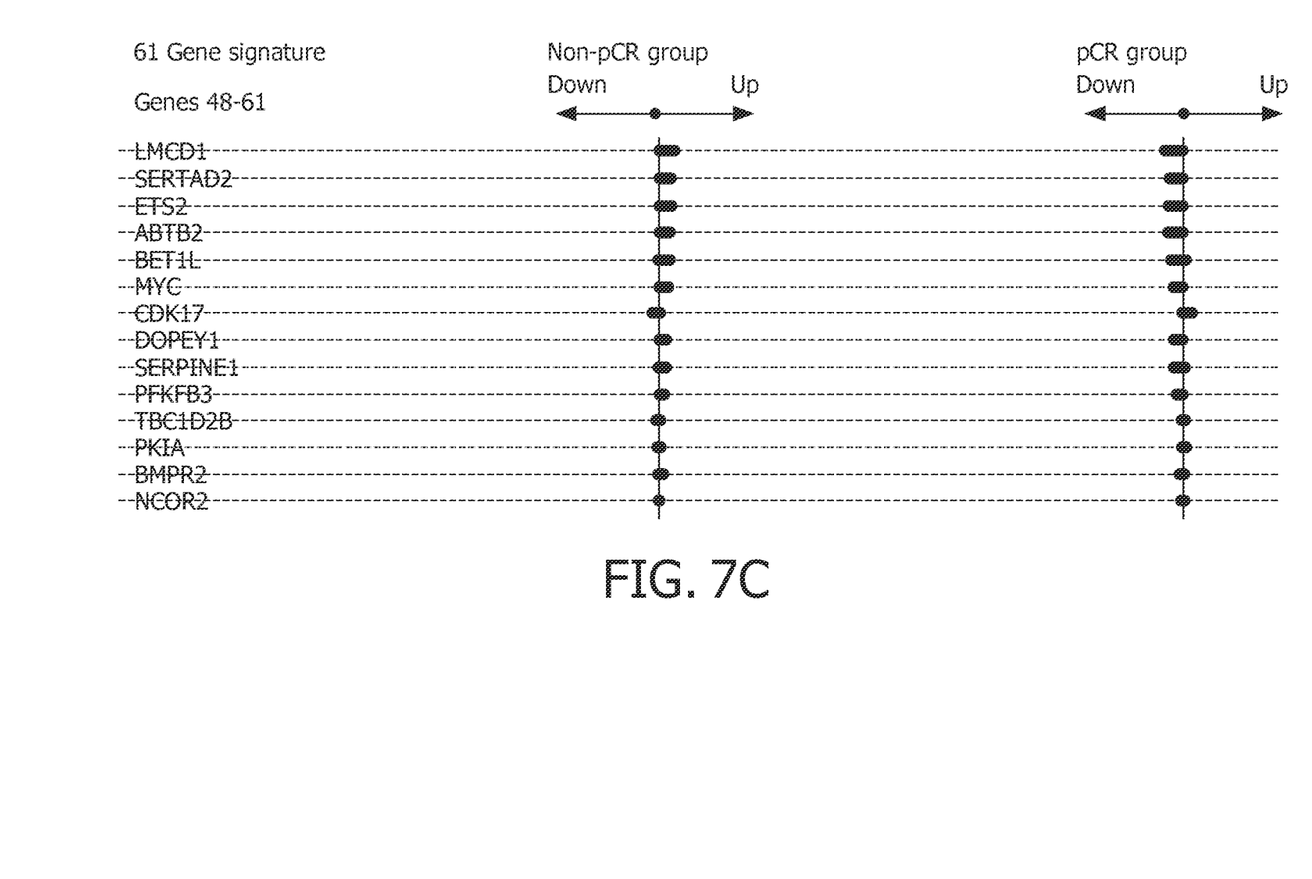

The trained shrunken centroid classifier (corresponding to trained classifier 64 of FIG. 3) operates on an input set of 61 genes listed in Table 1 and in FIGS. 7A, 7B, and 7C, where the listed genes are as defined in a standard resource called RefSeq. In Table 1, the 61 genes are listed along with the level of association provided by the shrunken centroid classifier for the "no pCR Group" and for the "pCR Group". The level of association is a metric of significance of the utility of that gene in the classifier.

TABLE 1

List of Genes in the illustrative 61-Gene Signature

| Centroid Classifier Gene | No_pCR Score | pCR Score |
| --- | --- | --- |
| CDKN2B | 0.4155 | −0.4847 |
| ATL2 | 0.3531 | −0.412 |
| CTGF | 0.3161 | −0.3688 |
| INHBA | 0.296 | −0.3453 |
| ID4 | 0.2839 | −0.3312 |
| BMPR1A | 0.2831 | −0.3303 |
| CD1E | −0.2805 | 0.3273 |
| TFDP1 | 0.2532 | −0.2954 |
| AMIGO2 | 0.2505 | −0.2923 |
| DDIT4 | 0.2408 | −0.2809 |
| TGFB2 | 0.2319 | −0.2705 |
| SPP1 | 0.2214 | −0.2583 |
| CD28 | −0.2157 | 0.2517 |
| PMEPA1 | 0.2137 | −0.2493 |
| FAT4 | −0.2132 | 0.2487 |
| KDM6B | −0.2071 | 0.2416 |
| MAP3K4 | 0.1667 | −0.1944 |
| FAM162A | 0.1652 | −0.1927 |
| MYH11 | −0.165 | 0.1925 |
| PPP2R1B | 0.1646 | −0.192 |
| LTBP1 | 0.1621 | −0.1891 |
| COL1A1 | −0.1583 | 0.1847 |
| YIPF5 | 0.1536 | −0.1792 |
| VEGFA | 0.1456 | −0.1699 |
| C18orf25 | 0.1416 | −0.1652 |
| FNDC3B | 0.131 | −0.1529 |
| MYBL1 | 0.1288 | −0.1503 |
| CDKN1A | 0.127 | −0.1481 |
| ARHGEF40 | −0.118 | 0.1376 |
| LARP6 | 0.1163 | −0.1357 |
| PAIP2B | 0.1116 | −0.1302 |
| RBMS1 | 0.1103 | −0.1287 |
| NR2F2 | −0.1024 | 0.1194 |
| ANGEL2 | 0.0976 | −0.1138 |
| LEMD3 | 0.0971 | −0.1133 |
| PPP2CA | 0.0958 | −0.1118 |
| NDST1 | −0.0895 | 0.1044 |
| ZNF395 | 0.0883 | −0.1031 |
| RNASE4 | 0.0877 | −0.1023 |
| SMURF1 | 0.0868 | −0.1012 |
| EDN1 | 0.0742 | −0.0866 |
| SSBP3 | 0.0726 | −0.0847 |
| SKIL | 0.0723 | −0.0843 |
| TBPL1 | 0.0703 | −0.082 |
| ALOX5AP | 0.0676 | −0.0789 |
| JUN | 0.0671 | −0.0783 |
| RARA | −0.0619 | 0.0722 |
| LMCD1 | 0.0589 | −0.0687 |
| SERTAD2 | 0.0419 | −0.0489 |
| ETS2 | 0.0417 | −0.0486 |
| ABTB2 | 0.04 | −0.0467 |
| BET1L | 0.0344 | −0.0402 |
| MYC | 0.032 | −0.0373 |
| CDK17 | −0.0316 | 0.0369 |
| DOPEY1 | 0.0236 | −0.0276 |
| SERPINE1 | 0.0236 | −0.0276 |
| PFKFB3 | 0.0157 | −0.0184 |
| TBC1D2B | −0.0157 | 0.0183 |
| PKIA | −0.0111 | 0.013 |
| BMPR2 | 0.0111 | −0.013 |
| NCOR2 | −0.0095 | 0.0111 |

The illustrative actually developed predictive outcome assessment test for the breast cancer therapy regimen diagrammatically shown in FIG. 1 employed the RNA sequencing data as the training data set for the classifier training operation 62. Accordingly, clinical use of this classifier is in accord with the approach of FIG. 4. RNA-sequencing data are acquired from patient tumor biopsy samples 70, 72 taken before and after the single dose 71 of bevacizumab. A HER2 negative patient who is to receive neoadjuvant bevacizumab in combination with chemotherapy will undergo a single biopsy to generate the first biopsy sample 70, and then receives a single dose 71 of bevacizumab monotherapy followed by a second biopsy to produce the second biopsy sample 72 taken from the tumor of the patient typically 10-15 days after receiving the bevacizumab monotherapy 71. RNA-sequencing is performed on both the tumor biopsies 70, 72 as per operations 24, 34 of FIG. 4. The differential gene expression analysis 74 is performed for the 61 genes in the TGF-p signature, including computing the log 2 fold-change values of the genes from baseline to postbrief-exposure and conversion into significance-adjusted log 2fc values as per operations 40, 42, 44 of FIG. 2 (but suitably performed only on the set of 61 genes that serve as input to the classifier). The vector of the 61-gene significance-adjusted log 2 fold change values is processed by the trained nearest-centroid classifier by comparing with the two centroids of the classifier, and the patient is assigned to the group associated with the nearest centroid, i.e. the group which shows significant down-regulation of TGFb activity or the group which shows significant up-regulation of TGFb activity. If the patient shows up-regulation of TGFb activity, the patient is unlikely to benefit from bevacizumab neoadjuvant treatment, and the pCR prediction is negative. On the other hand, if the patient shows down-regulation of TGFb activity, the patient is like to benefit from bevacizumab neoadjuvant treatment, and the pCR prediction is positive.

In a validation framework, this set of genes can be further refined based on correlation with RT-PCR data from the same samples. When RT-PCR is performed on the same samples as RNAseq, a mapping function is suitably employed to map the values from RNAseq to RT-PCR values. This could be a linear scaling function for all the genes or a higher order function (e.g. quadratic). Alternatively, the genes that correlate very well and for which linear mapping can be derived between RNAseq and RT_PCR, can be used in the final signature that is implemented using RT-PCR.

As described, the actually developed classifier can be used for identifying patients that can benefit from bevacizumab in the neoadjuvant setting. By extension, the classifier can be used as a companion diagnostic for bevacizumab. In some contemplated embodiments, the actually developed classifier is contemplated to be implemented as a module within PAPAyA, i.e. as an "in-silico" assay, which is a framework for integrating patient sequencing data for enabling clinical decision support in oncology. See Janevski et al., "PAPAyA: a platform for breast cancer biomarker signature discovery, evaluation and assessment", BMC Bioinformatics vol. 10 (Suppl 9):S7 (2009) (doi: 10.1186/1471-2105-10-S9-S7).

The 61-gene signature of Table 1 and FIGS. 7A, 7B, and 7C is a specific example which employs an input set of genes including all sixty-one genes listed in Table 1 (or equivalently in FIGS. 7A, 7B, and 7C). Numerous variants are contemplated.

For example, in some embodiments the gene signature employs an input set of genes including at least two genes of the group consisting of CDKN2B, ATL2, CTGF, INHBA, ID4, BMPR1A, CD1E, TFDP1, AMIGO2, DDIT4, TGFB2, SPP1, CD28, PMEPA1, FAT4, KDM6B, MAP3K4, FAM162A, MYH11, and PPP2R1B (i.e. at least two of the top twenty most informative genes of the illustrative 61 gene signature.

In other embodiments the gene signature employs an input set of genes including at least three genes of the group consisting of CDKN2B, ATL2, CTGF, INHBA, ID4, BMPR1A, CD1E, TFDP1, AMIGO2, DDIT4, TGFB2, SPP1, CD28, PMEPA1, FAT4, KDM6B, MAP3K4, FAM162A, MYH11, and PPP2R1B (i.e. at least three of the top twenty most informative genes of the illustrative 61 gene signature).

In other embodiments the gene signature employs an input set of genes including at least three genes of the group consisting of CDKN2B, ATL2, CTGF, INHBA, ID4, BMPR1A, CD1E, TFDP1, AMIGO2, DDIT4, TGFB2, SPP1, CD28, PMEPA1, FAT4, KDM6B, MAP3K4, FAM162A, MYH11, and PPP2R1B (i.e. at least three of the top twenty most informative genes of the illustrative 61 gene signature).

In other embodiments the gene signature employs an input set of genes including at least CDKN2B, ATL2, CTGF, INHBA, ID4, BMPR1A, CD1E, TFDP1, AMIGO2, and DDIT4 (i.e. at least the top ten most informative genes of the illustrative 61 gene signature).

In some embodiments, a pathway viewpoint is considered, and the gene signature employs an input set of genes belonging to the TGF-β signaling pathway. In some such embodiments, the input set of genes belonging to the TGF-β signaling pathway includes at least CDKN2B, INHBA, ID4, BMPR1A, CD1E, TFDP1, TGFB2, PPP2R1B, LTBP1, and PPP2CA. These genes were found in both the Mann-Whitney approach and belong to the illustrative 61-gene signature of Table 1 and FIGS. 7A, 7B, and 7C. In another embodiment, the input set of genes belonging to the TGF-β signaling pathway includes at least three genes of the group CDKN2B, INHBA, ID4, BMPR1A, CD1E, TFDP1, TGFB2, PPP2R1B, LTBP1, and PPP2CA. In some embodiments the input set of genes belonging to the TGF-β signaling pathway includes at least 61 genes belonging to the TGF-β signaling pathway.

The actually developed predictive outcome assessment test is an illustrative example. More generally, the test development approaches described herein with reference to FIGS. 2 and 3 are suitably applied to predict pCR for any oncological treatment regimen that includes a neoadjuvant therapeutic agent such as bevacizumab in combination with any chemotherapeutic agent such as cisplatin, carboplatin, nab-paclitaxel, docetaxel, or so forth. As disclosed herein, baseline and response biopsy samples are acquired for each study subject of a population before and after administration of the initial dose of the neoadjuvant therapeutic agent. The baseline and response biopsy samples are processed to generate baseline gene expression level information and response gene expression level information respectively for a large number of genes, e.g. at least 1000 genes, and more preferably at least 10,000 genes, and differential gene expression level information are calculated for each study subject comparing the baseline gene expression level information and the response gene expression level information. A classifier is then suitably trained using the differential gene expression level information calculated for the study subjects of the population as training data to generate a trained classifier that outputs a pCR prediction computed based on received differential gene expression level information for an input set of genes.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

The invention claimed is:
1. A method comprising:
providing a trained classifier configured to generate, from differential gene expression level information obtained from a patient's breast tumor, a pathological complete response (pCR) prediction, wherein the trained classifier is trained with differential gene expression level information calculated for a plurality of study subjects;
acquiring a baseline sample of a breast tumor of a patient, the baseline sample acquired before initiating a breast cancer therapy regimen to the patient;

determining, from the acquired baseline sample, baseline gene expression level information for a predetermined input set of genes comprising a first set of genes, wherein the baseline gene expression level information is generated by one or more of ribonucleic acid (RNA) sequencing, reverse transcription-polymerase chain reaction (RT-PCR) processing, and microarray processing;

acquiring a response sample of the same breast tumor of the patient, the response sample acquired 10-14 days after administration of the breast cancer therapy regimen comprising at least a first dose bevacizumab to the patient;

determining, from the acquired response sample, response gene expression level information for the predetermined input subset of genes, wherein the baseline gene expression level information is generated by one or more of ribonucleic acid (RNA) sequencing, reverse transcription-polymerase chain reaction (RT-PCR) processing, and microarray processing;

generating differential expression level information for the predetermined input subset of genes, the differential gene expression level information comparing:
(i) the determined baseline gene expression level information; and
(ii) the determined response gene expression level information;

computing, via the trained classifier, a pathological complete response (pCR) prediction for the patient based on the differential gene expression level information for the input subset of genes;

determining, by a physician treating the patient, based on the computed pCR prediction for the patient, whether to: (i) continue a bevacizumab regimen; or (ii) modify the bevacizumab regimen; and treating the patient by: (i) continuing the bevacizumab regimen; or (ii) modifying the bevacizumab regimen;

wherein the generating and computing are performed by an electronic data processing device comprising the trained classifier; and wherein the first set of genes comprises CDKN2B, ATL2, CTGF, INHBA, ID4, BMPR1A, CD1E, TFDP1, AMIGO2, DDIT4, TGFB2, SPP1, CD28, PMEPA1, FAT4, KDM6B, MAP3K4, FAM162A, MYH11, PPP2R1B, LTBP1, COL1A1, YIPF5, VEGFA, C18orf25, FNDC3B, MYBL1, CDKN1A, ARHGEF40, LARP6, PAIP2B, RBMS1, NR2F2, ANGEL2, LEMD3, PPP2CA, NDST1, ZNF395, RNASE4, SMURF1, EDN1, SSBP3, SKIL, TBPL1, ALOX5AP, JUN, RARA, LMCD1, SERTAD2, ETS2, ABTB2, BET1L, MYC, CDK17, DOPEY1, SERPINE1, PFKFB3, TBC1D2B, PKIA, BMPR2, and NCOR2.

2. The method of claim 1 wherein the breast cancer therapy regimen further includes administering at least one chemotherapy agent in addition to bevacizumab.

3. The method of claim 1, wherein the initiating comprises administering the first dose of bevacizumab to the patient without administering another chemotherapy agent to the patient.

4. The method of claim 1, wherein the wherein the predetermined input set of genes consists of CDKN2B, ATL2, CTGF, INHBA, ID4, BMPR1A, CD1E, TFDP1, AMIGO2, DDIT4, TGFB2, SPP1, CD28, PMEPA1, FAT4, KDM6B, MAP3K4, FAM162A, MYH11, PPP2R1B, LTBP1, COL1A1, YIPF5, VEGFA, C18orf25, FNDC3B, MYBL1, CDKN1A, ARHGEF40, LARP6, PAIP2B, RBMS1, NR2F2, ANGEL2, LEMD3, PPP2CA, NDST1, ZNF395, RNASE4, SMURF1, EDN1, SSBP3, SKIL, TBPL1, ALOX5AP, JUN, RARA, LMCD1, SERTAD2, ETS2, ABTB2, BET1L, MYC, CDK17, DOPEY1, SERPINE1, PFKFB3, TBC1D2B, PKIA, BMPR2, and NCOR2.

5. The method of claim 1, wherein the computing of the pCR prediction comprises inputting the input subset of genes to the trained classifier.

6. The method of claim 1, wherein the trained classifier is a shrunken centroid classifier.

7. A method comprising:
generating differential gene expression level information comparing:
(i) baseline gene expression level information from a baseline sample of a breast tumor of a patient acquired before initiating a breast cancer therapy regimen to the patient; and
(ii) response gene expression level information from a response sample of the breast tumor acquired after initiating the breast cancer therapy regimen by administering of bevacizumab to the patient for an input set of genes, at least some of the input set of genes belonging to the transforming growth factor 13 (TGF-β) signaling pathway;

computing a pathological complete response (pCR) prediction for the patient based on the differential gene expression level information for the input set of genes;

computing, via a trained classifier, a pathological complete response (pCR) prediction for the patient based on the differential gene expression level information for the input subset of genes, wherein the trained classifier is trained with differential gene expression level information calculated for a plurality of study subjects;

determining, by a physician treating the patient, based on the computed pCR prediction for the patient, whether to: (i) continue a bevacizumab regimen; or (ii) modify the bevacizumab regimen; and treating the patient by: (i) continuing the bevacizumab regimen; or (ii) modifying the bevacizumab regimen;

wherein the input set of genes comprises at least CDKN2B, ATL2, CTGF, INHBA, ID4, BMPR1A, CD1 E, TFDP1, AMIGO2, DDIT4, TGFB2, SPP1, CD28, PMEPA1, FAT4, KDM6B, MAP3K4, FAM162A, MYH11, PPP2R1B, LTBP1, COL1A1, YIPF5, VEGFA, C18orf25, FNDC3B, MYBL1, CDKN1A, ARHGEF40, LARP6, PAIP2B, RBMS1, NR2F2, ANGEL2, LEMD3, PPP2CA, NDST1, ZNF395, RNASE4, SMURF1, EDN1, SSBP3, SKIL, TBPL1, ALOX5AP, JUN, RARA, LMCD1, SERTAD2, ETS2, ABTB2, BET1L, MYC, CDK17, DOPEY1, SERPINE1, PFKFB3, TBC1D2B, PKIA, BMPR2, and NCOR2.

8. A method comprising:
initiating an breast cancer therapy regimen comprising at least bevacizumab by administering a first dose of bevacizumab to a patient;
before the initiating, acquiring a baseline sample of a malignant tumor in the patient;
after the initiating, acquiring a response sample of the malignant tumor in the patient;
generating baseline gene expression level information from the baseline sample for an input set of genes;
generating response gene expression level information from the response sample for the input set of genes;
generating differential gene expression level information comparing the baseline and response gene expression level information for the input set of genes;

computing, via a trained classifier, a pathological complete response (pCR) prediction for the patient based on the differential gene expression level information for the input set of genes, wherein the trained classifier is trained with differential gene expression level information calculated for a plurality of study subjects;

determining, by a physician treating the patient, based on the computed pCR prediction for the patient, whether to: (i) continue the breast cancer therapy regimen; or (ii) modify the breast cancer therapy regimen; and treating the patient by: (i) continuing the breast cancer therapy regimen; or (ii) modifying the breast cancer therapy regimen;

wherein the input set of genes comprises at least CDKN2B, ATL2, CTGF, INHBA, ID4, BMPR1A, CD1 E, TFDP1, AMIGO2, DDIT4, TGFB2, SPP1, CD28, PMEPA1, FAT4, KDM6B, MAP3K4, FAM162A, MYH11, PPP2R1B, LTBP1, COL1A1, YIPF5, VEGFA, C18orf25, FNDC3B, MYBL1, CDKN1A, ARHGEF40, LARP6, PAIP2B, RBMS1, NR2F2, ANGEL2, LEMD3, PPP2CA, NDST1, ZNF395, RNASE4, SMURF1, EDN1, SSBP3, SKIL, TBPL1, ALOX5AP, JUN, RARA, LMCD1, SERTAD2, ETS2, ABTB2, BET1L, MYC, CDK17, DOPEY1, SERPINE1, PFKFB3, TBC1D2B, PKIA, BMPR2, and NCOR2.

9. The method of claim 8 wherein the oncological breast cancer therapy regimen further includes at least one chemotherapy agent in addition to bevacizumab.

10. The method of claim 9, wherein the initiating comprises:
initiating the breast cancer therapy regimen by administering the first dose of bevacizumab to the patient without administering the at least one additional chemotherapy agent to the patient.

11. The method of claim 7 wherein the baseline and response gene expression level information are messenger ribonucleic acid (mRNA) level information or protein level information, and the differential gene expression level information is one of differential mRNA level information and differential protein level information.

12. A method comprising:
for each study subject of a population of study subjects:
initiating an oncological therapy regimen including at least a neoadjuvant therapeutic agent by administering a first dose of the neoadjuvant therapeutic agent to the study subject;
before the initiating, acquiring a baseline sample of a malignant tumor in the study subject;
after the initiating, acquiring a response sample of the malignant tumor in the study subject;
after acquiring the response sample, completing the oncological therapy regimen for the study subject;
after completing the oncological therapy regimen, determining pathological complete response (pCR) status of the study subject;
processing the baseline and response samples to generate baseline gene expression level information and response gene expression level information respectively for a plurality of genes; and
calculating differential gene expression level information for the study subject comparing the baseline gene expression level information and the response gene expression level information;

training a classifier using the differential gene expression level information calculated for the study subjects of the population as training data to generate a trained classifier that outputs a pCR prediction computed based on received differential gene expression level information for an input set of genes;

determining, by the trained classifier, a pCR prediction for an oncological patient based on differential gene expression level information from the patient;

determining, by a physician treating the oncological patient, based on the computed pCR prediction for the patient, whether to: (i) continue the oncological therapy regimen; or (ii) modify the oncological therapy regimen; and treating the patient by: (i) continuing the oncological therapy regimen; or (ii) modifying the oncological therapy regimen;

wherein the plurality of genes comprises at least CDKN2B, ATL2, CTGF, INHBA, ID4, BMPR1A, CD1 E, TFDP1, AMIGO2, DDIT4, TGFB2, SPP1, CD28, PMEPA1, FAT4, KDM6B, MAP3K4, FAM162A, MYH11, PPP2R1B, LTBP1, COL1A1, YIPF5, VEGFA, C18orf25, FNDC3B, MYBL1, CDKN1A, ARHGEF40, LARP6, PAIP2B, RBMS1, NR2F2, ANGEL2, LEMD3, PPP2CA, NDST1, ZNF395, RNASE4, SMURF1, EDN1, SSBP3, SKIL, TBPL1, ALOX5AP, JUN, RARA, LMCD1, SERTAD2, ETS2, ABTB2, BET1L, MYC, CDK17, DOPEY1, SERPINE1, PFKFB3, TBC1D2B, PKIA, BMPR2, and NCOR2.

* * * * *